United States Patent [19]
Thiede et al.

[11] Patent Number: 6,030,836
[45] Date of Patent: Feb. 29, 2000

[54] VITRO MAINTENANCE OF HEMATOPOIETIC STEM CELLS

[75] Inventors: Mark A. Thiede, Forest Hill; Mark F. Pittenger, Severna Park; Gabriel Mbalaviele, Columbia, all of Md.

[73] Assignee: Osiris Therapeutics, Inc., Baltimore, Md.

[21] Appl. No.: 09/327,840

[22] Filed: Jun. 8, 1999

Related U.S. Application Data

[60] Provisional application No. 60/088,431, Jun. 8, 1998.
[51] Int. Cl.$^7$ ................ C12N 5/08; C12N 5/10
[52] U.S. Cl. ................................ 435/347; 435/455
[58] Field of Search ................... 435/325, 347; 514/44

[56] References Cited

PUBLICATIONS

Stem Cells 15: 303–313, 1997. Koller, MR et al., Importance of parenchymal:stromal cell ratio for the ex vivo reconstitution of human hematopoiesis.

J. Cell. Physiology 165: 386–397, 1995. Dooley, DC et al., Basic fibroblast growth factor and epidermal growth factor downmodulate the growth of hematopoietic cells in long-term stromal cultures.

Verma, I and Somia, N, Nature 389:239–242 (1997), Oct. 22, 1999.

Report and Recommendations of the Panel to Assess the NIH Investment in Research on Gene Therapy. Orkin, S, and Motulsky, A., (www.nih.gov/news/panelrep.html) 1995, Oct. 22, 1999.

*Primary Examiner*—John S. Brusca
*Assistant Examiner*—Andrea Ousley
*Attorney, Agent, or Firm*—Elliot M. Olstein; Raymond J. Lillie

[57] ABSTRACT

The present invention is directed to human mesenchymal stem cells isolated from a tissue specimen, such as marrow cells, and to the method of co-culturing isolated mesenchymal stem cells and/or mesenchymal stem cell-derived adipocytes with hematopoietic progenitor cells such that the hematopoietic stem cells retain their phenotype.

25 Claims, 5 Drawing Sheets

VITRO MAINTENANCE OF HEMATOPOIETIC STEM CELLS

This Application claims the benefit of U.S. Provisional No. 60/088,431 filed Jun. 8, 1998.

The present invention relates to hematopoietic stem cells and more particularly to a process and composition for maintaining human hematopoietic stem cells to reduce or eliminate differentiation of human hematopoietic stem cells into a committed lineage.

BACKGROUND OF THE INVENTION

The maintenance of progenitor hematopoietic stem cells in culture is known to be dependent on the presence of a mixed population of stromal cells which provides an adherent layer upon which the stem cells reside and produces the different signals required for proliferation, self-renewal and differentiation of the hematopoietic stem cells into various hematopoietic lineages. Diverse cell types including stromal cells and adipocytes which arise from mesenchymal stem cells (MSCs) are present in bone marrow.

It is desirable in certain circumstances to maintain progenitor hematopoietic stem cells, such as CD34+ cells, in culture such that the cells proliferate and a majority of the cells retain their CD34+ phenotype.

It is further advantageous to maintain the hematopoietic stem cells such that, if differentiation does occur, differentiation will be along selected hematopoietic cell lineages, such as monocytes, osteoclasts or other cell types.

SUMMARY OF THE INVENTION

In accordance with one aspect of the present invention, there is provided a process and composition for maintaining human hematopoietic stem cells wherein the cells are co-cultured with human mesenchymal stem cells or adipocytes. The adipocytes may be derived from human mesenchymal stem cells. Applicants have found that such co-culturing is useful for maintaining the progenitor CD34+ phenotype for such hematopoietic stem cells.

In accordance with another aspect of the present invention, there is provided a process and composition for maintaining human hematopoietic stem cells in co-culture with human mesenchymal stem cells such that the CD34+/Thy1+ phenotype for such hematopoietic stem cells is maintained.

In a particular embodiment of the invention, the adipocytes are derived from human mesenchymal stem cells.

In another aspect of the invention the human hematopoietic stem cells are genetically modified to carry within them genes of interest particularly for the expression of physiologically or pharmacologically active proteins.

BRIEF DESCRIPTION OF THE DRAWINGS

FIG. 2A shows that the CD34+ cell phenotype is maintained throughout the coculture period.

FIG. 2B shows that the CD34+/CD14+ cell phenotype was increased.

FIG. 2C shows that the CD34+/CD90+ cell phenotype was slightly increased.

FIG. 4A shows that the CD34+ cell phenotype was maintained at day 14 and was decreased by 25% at day 21.

FIG. 4B shows that the CD34+/CD14+ cell phenotype was increased at day 14 and 21 in CD34+ cell cocultured with MSC-derived adipocytes over that obtained with MSCs.

FIG. 4C shows that the CD34+/CD90+ cell phenotype was increased at day 14 and 21 in CD34+ cells cocultured with both MSCs and MSC-derived adipocytes.

DETAILED DESCRIPTION OF THE INVENTION

Figure 1:
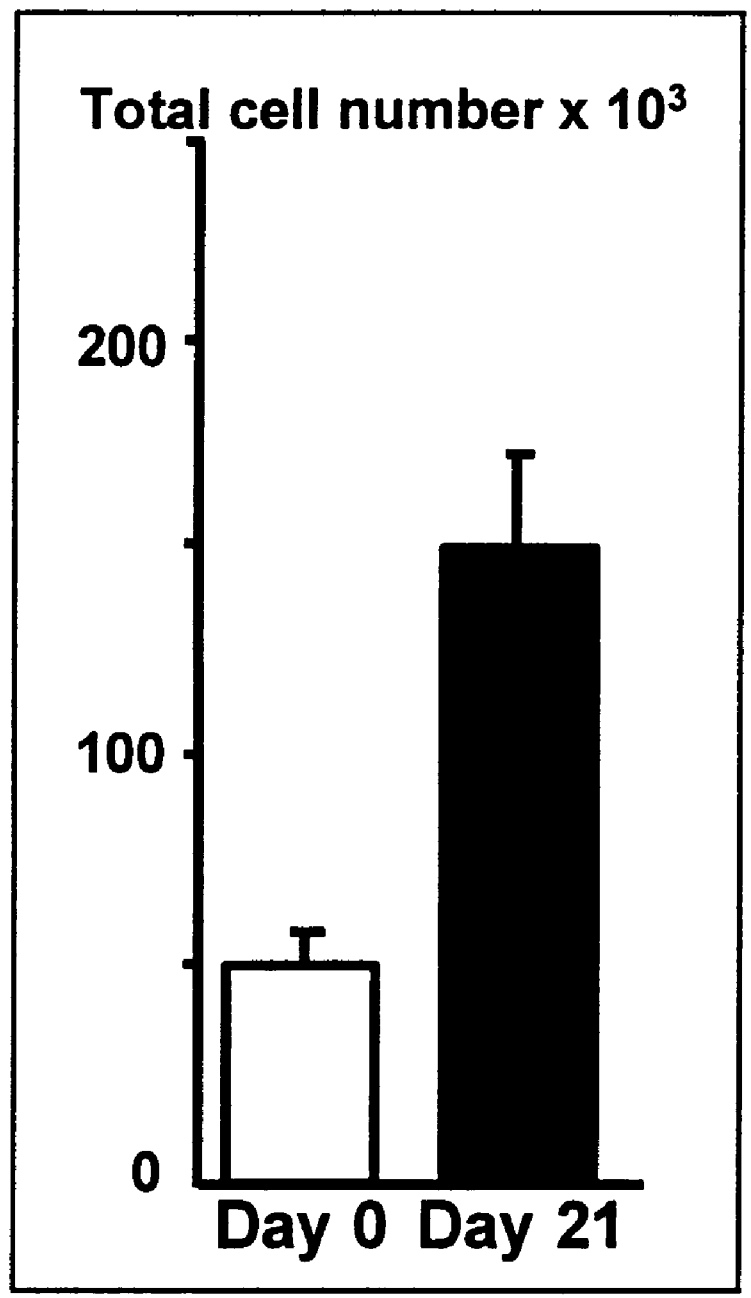
FIG. 1 illustrates the growth and maintenance of a total hematopoietic CD34+ population in co-culture with human mesenchymal stem cells.

The present invention relates generally to the use of human mesenchymal stem cells to support the maintenance of human CD34+ stem cells and to compositions comprising human CD34+ cells and human mesenchymal stem cells.

In particular, applicants have found that human mesenchymal stem cells (hMSCs) used in culture as a feeder layer in association with CD34+ cells are useful for maintaining the CD34+ cells expressing low or high levels of CD14 or CD90. CD90 is also known as Thy1. Thus, a CD34+ cell population can proliferate, be maintained and utilized, for example, as a source of hematopoietic progenitor cells for bone marrow transplantation and regeneration.

In one embodiment, the present invention relates to the use of mesenchymal stem cell-derived adipocytes to support the maintenance of human CD34+ stem cells and to compositions comprising human CD34+ cells, human mesenchymal stem cells and/or mesenchymal stem cell-derived adipocytes.

In particular, applicants have found that human mesenchymal stem cells (hMSCs) or adipocytes used in culture as a feeder layer in association with CD34+ cells are useful for maintaining the CD34+ cells expressing low or high levels of CD14 or CD90. The adipocytes may be mesenchymal stem cell-derived. Thus, a CD34+ cell population can proliferate, be maintained and utilized, for example, as a source of hematopoietic progenitor cells for bone marrow transplantation and regeneration.

The inventors herein demonstrate successful hematopoietic cell maintenance and growth under suitable in vitro conditions in the presence of human mesenchymal stem cells or mesenchymal stem cell-derived adipocytes.

According to the methods of the invention, when the mesenchymal stem cells or mesenchymal stem cell-derived adipocytes are co-cultured with the hematopoietic stem cells, the mesenchymal cells support the growth of the hematopoietic stem cells in a manner such that differentiation of the progenitor CD34+ cells and the loss of the CD34+ phenotype is reduced and greater stem cell potential is maintained.

According to the method of the present invention, the isolated mesenchymal stem cells or mesenchymal stem cell-derived adipocytes and the isolated hematopoietic progenitor cells, preferably CD34+ cells, are each culture expanded in appropriate media, i.e. cultured by methods using conditions that are apparent to those of skill in the art which favor cell growth, and production of homogeneous cell populations.

The mesenchymal stem cell or mesenchymal stem cell-derived adipocyte cell populations and the hematopoietic progenitor cells are then co-cultured in a medium that promotes the growth of the human mesenchymal cells and does not adversely affect the maintenance of the hematopoietic stem cells. Suitable media for example are described in U.S. Pat. No. 5,486,359.

In a preferred embodiment, the mesenchymal stem cell or mesenchymal stem cell-derived adipocyte cell populations and the hematopoietic stem cells are co-cultured in a human mesenchymal stem cell medium, Dulbecco's Modified Eagles Medium (DMEM-LG #11885 Life Technologies, Gaithersburg, Md.). The medium preferably contains an amount of serum which maintains the human mesenchymal stem cells. It has been discovered that using this medium allows the human mesenchymal cells to sustain the CD34+ cell population and thereby reduces the loss of stem cells which include the primitive phenotype (CD34+Thy1+) that is characteristic of early stage human hematopoietic stem cells.

Accordingly, for purposes of the present invention, the culture medium contains serum, for example, fetal bovine serum, that most preferably is at a concentration of at least 5%. The serum concentration can be at a concentration of up to about 25%; and is preferably at a concentration which does not exceed 20%.

The culture conditions such as temperature, pH, and the like, are those previously used with human mesenchymal stem cells or mesenchymal stem cell-derived adipocytes and hematopoietic stem cells utilized in this invention and will be apparent to one of skill in the art.

In order to obtain subject human mesenchymal stem cells for the methods described herein, mesenchymal stem cells can be recovered from bone marrow or other mesenchymal stem cell sources. Bone marrow cells may be obtained from iliac crest, femora, tibiae, spine, rib or other medullary spaces. Other sources of human mesenchymal stem cells include embryonic yolk sac, placenta, umbilical cord, fetal and adolescent skin, and blood. The presence of mesenchymal stem cells in the culture colonies may be verified by specific cell surface markers which are identified with monoclonal antibodies, see, e.g., U.S. Pat. No. 4,586,359. These isolated mesenchymal cell populations display epitopic characteristics associated only with mesenchymal stem cells, have the ability to proliferate in culture without differentiating, and have the ability to differentiate into specific mesenchymal lineages when either induced in vitro or in vivo at the site of damaged tissue.

The human mesenchymal stem cell or mesenchymal stem cell-derived adipocyte populations can be allogeneic, or not donor matched, to the hematopoietic stem cells, or the mesenchymal cells can be autologous to the hematopoietic stem cells.

Accordingly, any process that is useful to recover mesenchymal stem cells from human tissue may be utilized to result in a population of cells comprising mostly mesenchymal stem cells. In one aspect, the method of isolating human mesenchymal stem cells comprises the steps of providing a tissue specimen containing mesenchymal stem cells, preferably bone marrow; isolating the mesenchymal stem cells from the specimen, for example, by density gradient centrifugation; adding the isolated cells to a medium which contains factors that stimulate mesenchymal stem cell growth without differentiation, and allows for the selective adherence of only the mesenchymal stem cells to a substrate surface in culture; culturing the specimen-medium mixture; and removing the non-adherent matter from the substrate surface, resulting in an isolated population of mesenchymal stem cells.

Mesenchymal stem cell-derived adipocytes can be obtained using methods for inducing differentiation of mesenchymal stem cells into adipocytes, described for example in U.S. Pat. No. 5,827,740.

In a further aspect of the present invention, any process that is useful to recover hematopoietic stem cells from human tissue may be utilized to result in a population of cells comprised mostly of hematopoietic cells. Stem cells can be recovered from various types of tissue such as bone marrow and blood, including peripheral blood. The human hematopoietic stem cells can be collected from bone marrow aspirates or peripheral blood and isolated using commercially available antibodies which bind to hematopoietic stem cell surface antigens, e.g. CD34, using methods known to those of skill in the art, see e.g. U.S. Pat. No. 4,714,680. For example, the antibodies may be conjugated to magnetic beads and immunogenic procedures utilized to recover the desired cell type.

The human mesenchymal stem cell and the hematopoietic cells are co-cultured under appropriate culture conditions such that the mesenchymal cells adhere to a substrate surface and form a monolayer. The mesenchymal stem cells are plated at a density in a range of from about $3 \times 10^3$ to about $5 \times 10^3$ cells per $cm^2$. Adipogenesis is induced as previously described after the mesenchymal stem cells have reached confluency. The CD34+ cells are preferably at a cell density of approximately $5 \times 10^4$ cells per $cm^2$.

The hematopoietic stem cells produced according to the methods described herein can be used to provide a reliable and constant source of hematopoietic stem cells for individuals in need thereof, e.g. those in need of transfusions of blood products or components, such as those individuals receiving chemotherapy or a bone marrow transplant.

Another aspect of the present invention relates to the introduction of foreign genes into the hematopoietic stem cells such that the hematopoietic stem cells carry the new genetic material and can express the desired gene product. Examples of genetic material for transduction into hematopoietic stem cells includes those which express gene products which have a role in hematopoietic stem cell maintenance, tissue development, remodeling, repair or in vivo production of extracellular gene products.

In accordance with this aspect of the invention, the hematopoietic stem cells can be modified with genetic material of interest (transduced or transformed or transfected). These modified cells can then be administered to a target tissue, e.g. bone marrow, where the expressed product will have a beneficial effect. The modified CD34+ cells can also be co-cultured in vitro with mesenchymal stem cells or mesenchymal stem cell-derived adipocytes.

Thus, genes can be introduced into cells which are then returned to the autologous donor or an allogeneic recipient where the expression of the gene will have a therapeutic effect. For example, hematopoietic stem cells may be genetically engineered to have an altered activity in vivo.

The hematopoietic stem cells may be genetically modified in the presence or absence of the human mesenchymal stem cells or mesenchymal stem cell-derived adipocytes.

The hematopoietic stem cells may be genetically modified by incorporation of genetic material into the cells, for example using recombinant expression vectors.

As used herein "recombinant expression vector" refers to a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription initiation and termination sequences. Structural units intended for use in eukaryotic expression systems preferably include a leader sequence enabling extracellular secretion of translated protein by a host cell. Alternatively, where recombinant protein is expressed without a leader or transport sequence, it may include an N-terminal methionine residue. This residue may or may not be subsequently cleaved from the expressed recombinant protein to provide a final product.

The human hematopoietic stem cells thus may have stably integrated a recombinant transcriptional unit into chromosomal DNA or carry the recombinant transcriptional unit as a component of a resident plasmid. Cells may be engineered with a polynucleotide (DNA or RNA) encoding a polypeptide ex vivo, for example. Cells may be engineered by procedures known in the art by use of a retroviral particle containing RNA encoding a polypeptide.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is MGIN, derived from murine embryonic stem cells.

The nucleic acid sequence encoding the polypeptide is under the control of a suitable promoter. Suitable promoters which may be employed include, but are not limited to, TRAP promoter, adenoviral promoters, such as the adenoviral major late promoter; the cytomegalovirus (CMV) promoter; the respiratory syncytial virus (RSV) promoter; the Rous Sarcoma promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs; ITRs; the β-actin promoter; and human growth hormone promoters. The promoter also may be the native promoter that controls the gene encoding the polypeptide. These vectors also make it possible to regulate the production of the polypeptide by the engineered progenitor cells. The selection of a suitable promoter will be apparent to those skilled in the art.

It is also possible to use vehicles other than retroviruses to genetically engineer or modify the hematopoietic stem cells. Genetic information of interest can be introduced by means of any virus which can express the new genetic material in such cells. For example, SV40, herpes virus, adenovirus, adeno-associated virus and human papillomavirus can be used for this purpose. Other methods can also be used for introducing cloned eukaryotic DNAs into cultured mammalian cells, for example, the genetic material to be transferred to stem cells may be in the form of viral nucleic acids.

In addition, the expression vectors may contain one or more selectable marker genes to provide a phenotypic trait for selection of transformed cells such as dihydrofolate reductase or neomycin resistance.

The hematopoietic stem cells may be transfected through other means known in the art. Such means include, but are not limited to transfection mediated by calcium phosphate or DEAE-dextran; transfection mediated by the polycation Polybrene; protoplast fusion; electroporation; liposomes, either through encapsulation of DNA or RNA within liposomes, followed by fusion of the liposomes with the cell membrane or, DNA coated with a synthetic cationic lipid can be introduced into cells by fusion.

The present invention further makes it possible to genetically engineer human hematopoietic stem cells in such a manner that they produce, in vitro or in vivo produce polypeptides, hormones and proteins not normally produced in human hematopoietic stem cells in biologically significant amounts or produced in small amounts but in situations in which regulatory expression would lead to a therapeutic benefit. For example, the hematopoietic stem cells could be engineered with a gene that expresses a molecule that specifically inhibits bone resorption. Alternatively the cells could be modified such that a protein normally expressed will be expressed at much lower levels. These products would then be secreted into the surrounding media or purified from the cells. The human hematopoietic stem cells formed in this way can serve as continuous short term or long term production systems of the expressed substance. These genes can express, for example, hormones, growth factors, matrix proteins, cell membrane proteins, cytokines, adhesion molecules, "rebuilding" proteins important in tissue repair. The expression of the exogenous genetic material in vivo, is often referred to as "gene therapy." Disease states and procedures for which such treatments have application include genetic disorders and diseases of bone and the immune system. Cell delivery of the transduced cells may be effected using various methods and includes infusion and direct depot injection into periosteal, bone marrow and subcutaneous sites.

In addition, as hereinabove described, the transduced cells may be used for in vitro production of desired protein(s). The transduced cells may further be used in screening assays for drug discovery.

The above description of the invention and the following examples are by way of illustration only. Other permutations and practices of the invention will be readily envisioned by one of ordinary skill in the art by view of the above in conjunction with the appended drawings. Therefore, such permutations and variations are within the scope of the present invention.

EXAMPLES

Human bone marrow aspirates used for the isolation of the mesenchymal stem cells and CD34+ cells were purchased from Poietic Technologies, Gaithersburg, Md.

Example 1

Human MSCs (hMSCs) were isolated and cultured according to known methods (e.g. U.S. Pat. No. 5,486,359). Heparinized bone marrow samples were collected from healthy human donors. Mononucleated cells were isolated using a 1.073 Percoll density gradient and placed into DMEM-LG (low glucose) medium supplemented with 10% FBS.

Adipogenic differentiation of MSCs was performed as described, for example, in U.S. Pat. No. 5,827,740.

CD34+ cells, isolated from bone marrow of healthy patients (Poietic Technologies, Inc., Gaithersburg, Md.) were purified to 95% purity using antibody to CD34 conjugated to magnetic beads (CD34+ cell separation column: Miltenyi Biotec, Auburn, Calif. Ab:QBEND.10) and cryopreserved.

CD34+ cells were seeded at 5×10⁴ cells per cm² onto layers of MSCs or MSC-derived adipocytes. Cocultures were maintained for 3 weeks at 37° C. in an atmosphere of 95% air/5% $CO_2$ and fed every three days with hMSC medium. Because most of the CD34+ cells remained non-adherent during the first 2 weeks, half of the culture medium was gently aspirated without agitating non-adherent cells and replaced with fresh medium.

Flow Cytometry Analysis

The hematopoietic cells were gently harvested using $Ca^{2+}$-$Mg^{2+}$ free Hank's Balanced Salt Solution (HBSS)-based buffer containing 5 mM EDTA. The total cell number was counted. FIG. 1 illustrates the growth and maintenance of a total hematopoietic CD34+ population in co-culture with human mesenchymal stem cells. The increase in total cell number in co-culture at day 21 was three-fold. Occasionally, MSCs were found in harvests but were not counted as they were morphologically recognizable. Uncultured cryopreserved CD34+ progenitor cells were used as a positive control. Approximately 2×10⁵ cells were incubated with 0.5% BSA to block nonspecific binding, then incubated with about 20 ug/ml of specific antibodies or control antibodies. Cells were analyzed for CD34+; CD34+/90+ (primitive hematopoietic cells); or CD34+/14+ (monocytes/macrophages) surface markers. Antibodies to CD34, CD90, CD14 were purchased from PharMingen Inc., San Diego, Calif. All incubations were performed at 4° C. for 30 minutes. Unbound antibodies were discarded by centrifugal washing. After incubation, 3 ml of PBS containing 0.5% BSA were added to the tubes which were then centrifuged for 5 minutes at 600×g. Samples were resuspended with 0.5 ml of the same buffer and immediately analyzed by flow cytometry. Background measurement was subtracted from the reading of each sample.

Colony Assay

The hematopoietic cells in co-culture with the MSCs or MSC-derived adipocytes were gently harvested at day 21 as described above. Cryopreserved CD34⁺ progenitors that were not cultured (i.e., cells were thawed and not placed into assay) were used as a positive control. Harvested cells were counted and mixed with MethoCult, a complete methylcellulose medium containing cytokines and erythropoietin (StemCell Technologies Inc., Vancouver, Canada) and plated according to manufacturer's protocol. Cultures were maintained for 2 weeks at 37° C. in 95% air/5% $CO_2$. The numbers of colonies which contained more than 100 cells were counted under light microscopy by manually scanning across the entire culture well in a systematic fashion.

Results

The results of the colony assay shown in Table 1 indicate that long term cocultures (LTC) with MSCs generated LTC-initiating cultures (LTC-IC).

TABLE 1

| Colony number per 1 × 10⁶ CD34⁺ cells | | |
|---|---|---|
| CFU-MG | CFU-E | Mix-CFU |
| 252 | 2 | 10 |

M macrophage; G granulocyte; E erythroid; CFU colony forming unit.

The total numbers of hematopoietic cell colonies (see Table 2) show that MSCs and MSC-derived adipocytes promote formation of LTC-IC.

TABLE 2

| Total colony number per 5 × 10⁵ CD34⁺ cells | |
|---|---|
| CD34 + cells + MSC coculture | 40 ± 15 |
| CD34 + cells + adipocyte coculture | 30 ± 2 |

Figure 2:
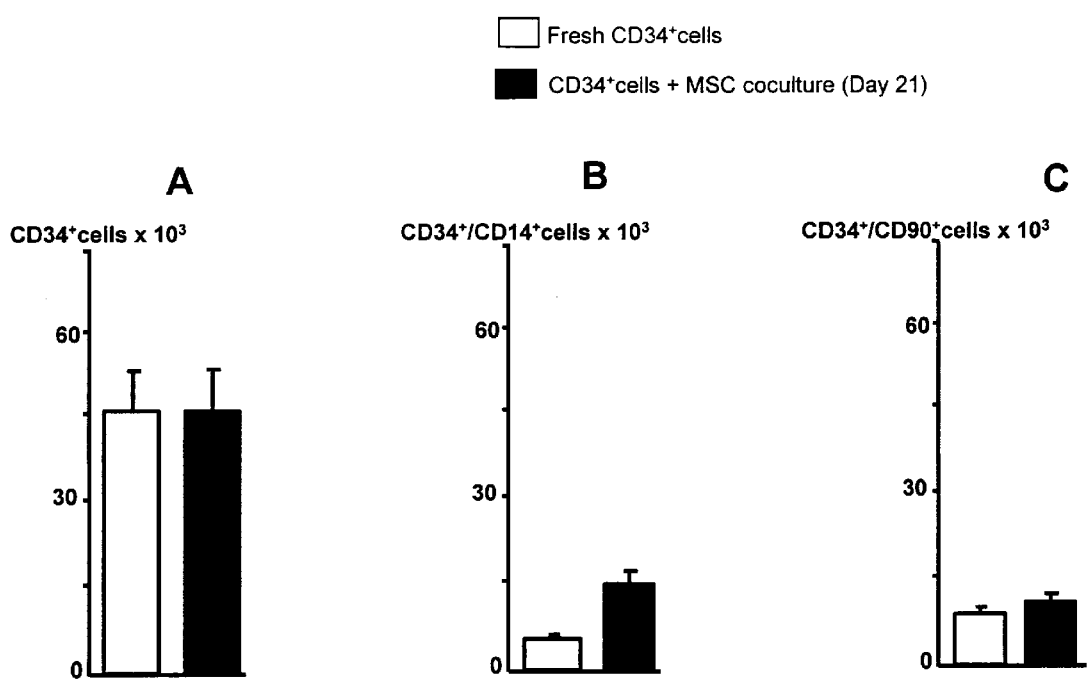
FIGS. 2A through 2C show the numbers of different hematopoietic cell phenotypes in the coculture as assayed by flow cytometry at day 21.

The results of the flow cytometry analysis of the cells in co-culture are shown in FIG. 2. At day zero, the expression of CD34+ (FIG. 2A), CD34+/14+ (FIG. 2B) and CD34+/90+ (FIG. 2B)) surface markers comprised approximately 90%, 7% and 13% of the cell population, respectively (of a total cell number 50×10³). After 21 days in co-culture, the cells in co-culture showed the expression of CD34 (FIG. 2A), CD34/14 (FIG. 2B) and CD34/90 (FIG. 2C) surface markers in approximately 30%, 9% and 7% of the cell population, respectively (of a total cell number 150×10³). The total absolute number of CD34+ cells was retained throughout the culture period, the total absolute number of CD34+/CD14+ cell phenotype was increased, while the total absolute number of CD34+/90+ cells was slightly increased.

Figure 3:
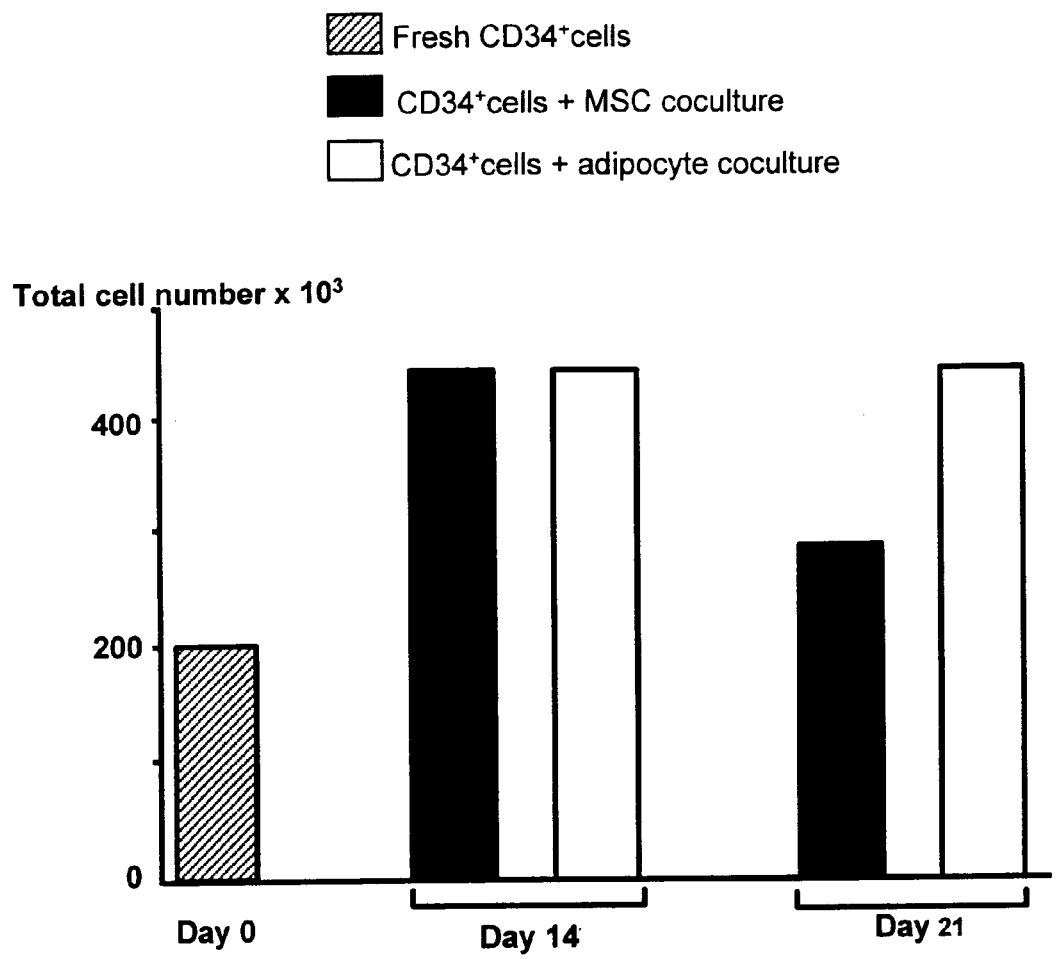
FIG. 3 shows the numbers of total hematopoietic cells in cocultures of CD34+ cells with MSCs or with MSC-derived adipocytes at day 14 and 21.

The total numbers of harvested hematopoietic cells at days 14 and 21 of CD34+ cells with MSCs or with MSC-derived adipocytes were determined. The data showed that MSCs or MSC-derived adipocytes promote the proliferation of CD34+ cells (FIG. 3).

Figure 4:
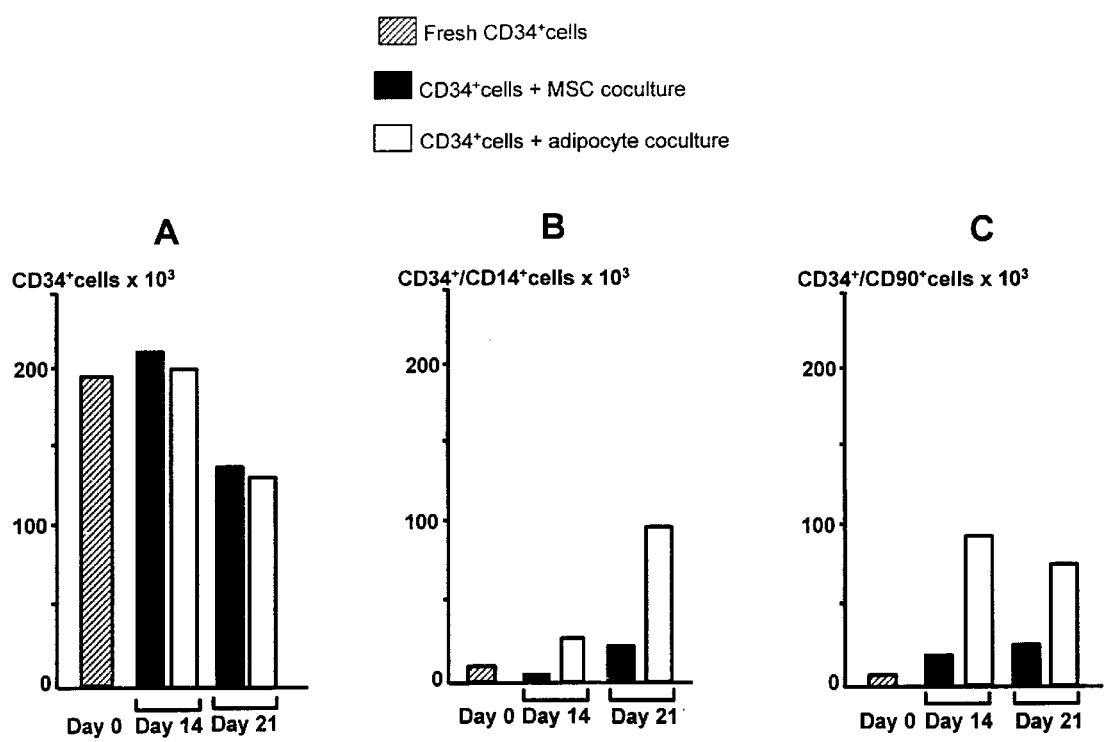
FIGS. 4A through 4C show the numbers of different hematopoietic cell phenotypes in CD34+ cells cocultured with MSCs or with MSC-derived adipocytes.

The numbers of different hematopoietic cell phenotypes in CD34+ cells cocultured with MSCs or with MSC-derived adipocytes at days 14 and 21 was measured (FIG. 4). The absolute number of CD34+ cells was retained during the first two weeks of coculture and then decreased by 25% at day 21 (FIG. 4A). The absolute number of cells with CD34+/CD14+ cell phenotype was increased at day 21 in coculture of CD34+ cells with MSCs and at both 14 and 21 in coculture of CD34+ cells with MSC derived adipocytes (FIG. 4B). The absolute number of cells with CD34+/CD90+ cell phenotype was increased at day 14 and 21 in CD34+ cells cocultured with both MSCs and MSC-derived adipocytes (FIG. 4C).

Figure 5:
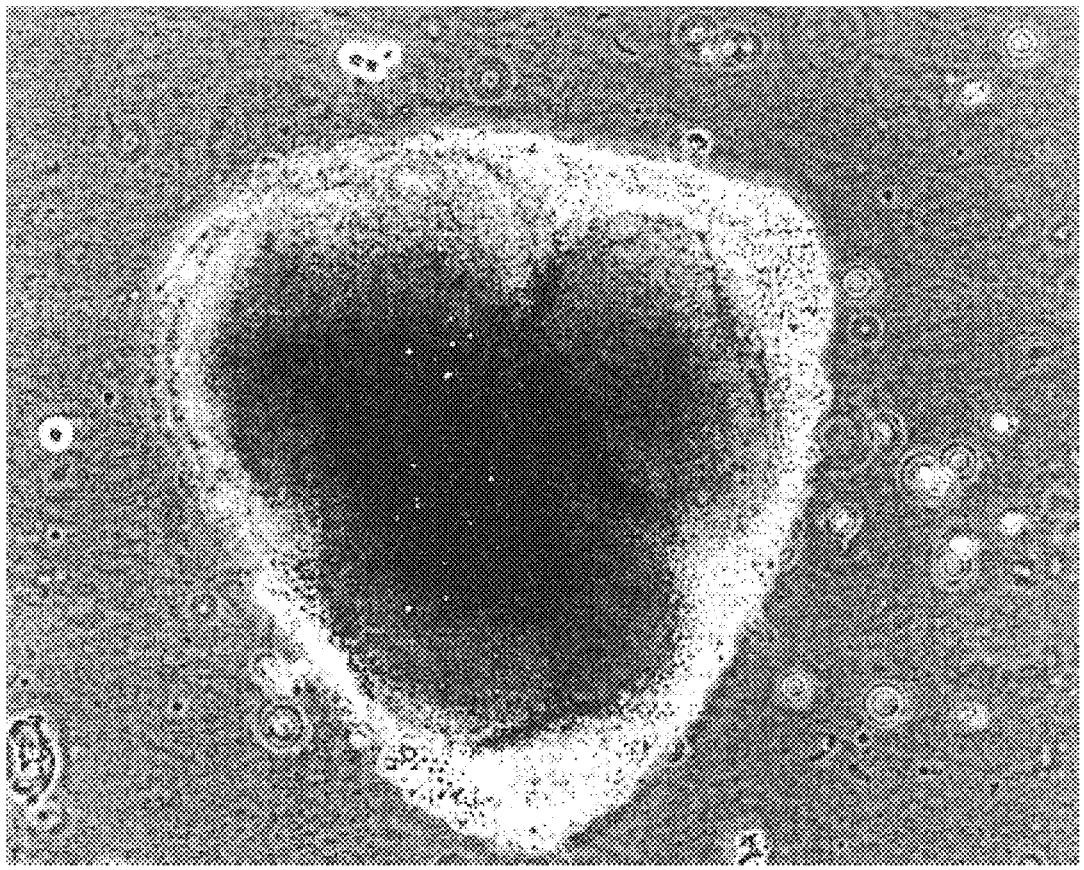
FIG. 5 is a photograph of colonies generated by hematopoietic cells originating from coculture of CD34+ cells with MSC-derived adipocytes.

FIG. 5 shows the morphology of colonies generated by hematopoietic cells that originated from coculture of CD34+ cells with MSC-derived adipocytes. Similar colonies were seen in coculture of CD34+ cells with MSCs.

These results demonstrate that primitive hematopoietic stem cells can be maintained in culture without losing their primitive hematopoietic stem cell phenotype. Thus, the method described herein is advantageous for expanding CD34+ cells in cultures for purposes of, for example, administering the cells to facilitate transplantation.

A number of modifications and variations of the present invention are possible in light of the above teachings and therefore, within the scope of the appended claims the invention may be practiced otherwise than as particularly described.

We claim:

1. A method of maintaining human hematopoietic stem cells in vitro comprising co-culturing human mesenchymal stem cells with the hematopoietic stem cells such that at least some of the hematopoietic stem cells maintain their stem cell phenotype.

2. The method of claim 1 wherein the hematopoietic stem cells are CD34+ cells.

3. The method of claim 1 wherein the mesenchymal stem cell population is allogeneic or autologous to the hematopoietic stem cell population.

4. A method of maintaining human hematopoietic stem cells in vitro comprising co-culturing adipocytes with the hematopoietic stem cells such that at least some of the hematopoietic stem cells maintain their stem cell phenotype.

5. The method of claim 4 wherein the adipocytes are derived from human mesenchymal stem cells.

6. The method of claim 4 wherein the hematopoietic stem cells are CD34+ cells.

7. The method of claim 4 wherein the adipocytes are allogeneic or autologous to the hematopoietic stem cell population.

8. A composition for maintaining human hematopoietic stem cells in vitro such that at least some of the hematopoietic stem cells retain their stem cell phenotype, comprising human hematopoietic stem cells and human mesenchymal stem cells.

9. A composition for maintaining human hematopoietic stem cells in vitro such that at least some of the hematopoietic stem cells retain the stem cell phenotype, comprising human hematopoietic stem cells and adipocytes.

10. The composition of claim 9 wherein the adipocytes are derived from human mesenchymal stem cells.

11. The composition of claim 9 wherein the hematopoietic stem cells are genetically modified.

12. The method of claim 3 wherein the mesenchymal stem cell population is allogeneic to the hematopoietic stem cell population.

13. The method of claim 3 wherein the mesenchymal stem cell population is autologous to the hematopoietic stem cell population.

14. The method of claim 1 wherein said human hematopoietic stem cells and said human mesenchymal stem cells are co-cultured in a culture medium which contains serum.

15. The method of claim 14 wherein said serum is present in said culture medium at a concentration of at least 5%.

16. The method of claim 15 wherein said serum is present in said culture medium at a concentration up to about 25%.

17. The method of claim 16 wherein said serum is present in said culture medium at a concentration that does not exceed 20%.

18. The method of claim 1 wherein said hematopoietic stem cells are genetically modified.

19. The method of claim 7 wherein the adipocytes are allogeneic to the hematopoietic stem cell population.

20. The method of claim 7 wherein the adipocytes are autologous to the hematopoietic stem cell population.

21. The method of claim 4 wherein said human hematopoietic stem cells and said adipocytes are co-cultured in a culture medium which contains serum.

22. The method of claim 21 wherein said serum is present in said culture medium at a concentration of at least 5%.

23. The method of claim 22 wherein said serum is present in said culture medium at a concentration up to about 25%.

24. The method of claim 23 wherein said serum is present in said culture medium at a concentration that does not exceed 20%.

25. The method of claim 4 who said hematopoietic stem cells are genetically modified.

* * * * *

UNITED STATES PATENT AND TRADEMARK OFFICE
CERTIFICATE OF CORRECTION

PATENT NO. : 6,030,836
DATED : February 29, 2000
INVENTOR(S) : Thiede, et. al.

It is certified that error appears in the above-indentified patent and that said Letters Patent is hereby corrected as shown below:

On the cover page, in the title, before "VITRO," insert - - IN - -.

At Column 1, in the title, before "VITRO," insert - - IN - -.

In Claim 25, change "who" to - - wherein - -.

Signed and Sealed this

Twentieth Day of March, 2001

Attest:

NICHOLAS P. GODICI

*Attesting Officer*    *Acting Director of the United States Patent and Trademark Office*